United States Patent [19]

Kühle et al.

[11] Patent Number: 4,562,208
[45] Date of Patent: Dec. 31, 1985

[54] N-SULPHENYLATED UREAS, MICROBICIDAL AGENTS CONTAINING THESE COMPOUNDS AND THEIR USE

[75] Inventors: Engelbert Kühle, Bergisch Gladbach; Wilfried Paulus; Hermann Genth, both of Krefeld; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 466,694

[22] Filed: Feb. 15, 1983

[30] Foreign Application Priority Data

Mar. 2, 1982 [DE] Fed. Rep. of Germany ....... 3207474

[51] Int. Cl.$^4$ ..................... C07C 145/04; A01N 47/28
[52] U.S. Cl. ............................. 514/593; 260/465 D; 514/522; 514/423; 564/39; 548/567
[58] Field of Search .......................... 564/39; 424/322; 514/593

[56] References Cited

U.S. PATENT DOCUMENTS 3,496,208  2/1970  Bachman et al. ................... 260/453
4,397,869  8/1983  Kühle et al. ...................... 564/39 X

FOREIGN PATENT DOCUMENTS 0046557  3/1982  European Pat. Off. .
1493603  9/1967  France .
2341567  9/1977  France .

OTHER PUBLICATIONS

Kühle et al., European Pat. Nos. 0 055 442, 07/07/82, 0 087 704, 09/07/83.

Primary Examiner—Thomas A. Waltz
Attorney, Agent, or Firm—Sprung, Horn, Kramer & Woods

[57] ABSTRACT

The new N-sulphenylated ureas can be prepared by reaction of the corresponding N-substituted carbamic acid-fluorides and a primary or secondary amine in the presence of a diluent and an acid-binding agent. They have microbicidal properties and can be used in particular for the protection of industrial materials and of plants.

4 Claims, No Drawings

N-SULPHENYLATED UREAS, MICROBICIDAL AGENTS CONTAINING THESE COMPOUNDS AND THEIR USE

The invention relates to new N-sulphenylated ureas, a process for their preparation, microbicidal agents containing these compounds and their use as microbicides, in particular for the protection of industrial materials and in plant protection.

The use of some N-(trihalogenomethylthio) compounds for the protection of industrial materials against microbial degradation is known (U.S. Pat. No. 2,563,770, *Journ. Agr. Food Chem.* 14, 365 (1966), *Fette, Seifen, Anstrichmittel (Fats, soaps, coating compositions)* 68, 272 (1966)). However, they are not always satisfactory since they are not effective against all microorganisms. In addition, they are poorly soluble in a coating and impregnation composition.

New N-sulphenylated ureas of the formula (I)

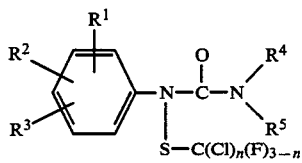

in which
$R^1$ to $R^3$ are identical or different and denote hydrogen, halogen, nitro, cyano, alkyl, alkoxy, alkylmercapto, trihalogenomethyl, trihalogenomethoxy or trihalogenomethylmercapto,
$R^4$ and $R^5$ can be identical or different and represent hydrogen, an optionally substituted alkyl, alkenyl, alkynyl or cycloalkyl radical, or together with the nitrogen atom form a 5-membered or 6-membered ring system which is optionally interrupted by a further heteroatom, and
n represents one of the numbers 0, 1, 2 or 3,
have been found.

The new N-sulphenylated ureas have an outstanding microbicidal action and are particularly suitable for the protection of industrial materials and in plant protection.

In accordance with the invention, halogen denotes, in general, fluorine, chlorine, bromine and iodine, preferably fluorine and chlorine.

In accordance with the invention, alkyl denotes in general, a straight-chain or branched hydrocarbon radical having 1 to 12, preferably 1 to 8, particularly preferably 1 to about 6 (lower alkyl), carbon atoms. The following alkyl radicals may be mentioned as examples: methyl, ethyl, propyl, isopropyl, butyl, isobutyl, pentyl, isopentyl, hexyl and isohexyl.

In accordance with the invention, alkoxy denotes, in general, a straight-chain or branched hydrocarbon radical, e.g. alkyl, which is bonded to oxygen and has 1 to 12, preferably 1 to 8, particularly preferably 1 to about 6 (lower alkoxy) carbon atoms. The following alkoxy radicals may be mentioned as examples: methoxy, ethoxy, propoxy, isopropoxy, butoxy, isobutoxy, pentoxy, isopentoxy, hexoxy and isohexoxy.

In accordance with the invention alkylmercapto denotes in general a straight-chain or branched hydrocarbon radical, e.g. alkyl, which is bonded to sulphur and has 1 to 18, preferably 1 to 8, in particular 1 to about 6 (lower alkylmercapto) carbon atoms. The following alkylmercapto radicals may be mentioned as examples: methylmercapto, ethylmercapto, propylmercapto, isopropylmercapto, butylmercapto, isobutylmercapto, pentylmercapto, isopentylmercapto, hexylmercapto and isohexylmercapto.

In accordance with the invention, trihalogenomethyl denotes in general a methyl radical which is substituted by three identical or different halogen atoms. In this case, halogen denotes in general fluorine, chlorine, bromine or iodine, preferably fluorine or chlorine.

In accordance with the invention, trihalogenomethoxy denotes in general a methoxy radical which is substituted by three halogen atoms. In this case, in accordance with the invention, halogen denotes in general fluorine, chlorine, bromine or iodine.

In accordance with the invention, trihalogenomethylmercapto denotes in general a methylmercapto radical which is substituted by three halogen atoms. In this case, halogen denotes in general fluorine, chlorine, bromine or iodine, preferably fluorine or chlorine.

In accordance with the invention, alkenyl denotes in general a straight-chain or branched hydrocarbon radical having 2 to 12, preferably 2 to 8, particularly preferably 2 to about 6 (lower alkenyl), carbon atoms with one or more, preferably one or two double bonds. The following alkenyl radicals may be mentioned as examples: allyl, pentenyl and octenyl.

In accordance with the invention, alkynyl denotes in general a straight-chain or branched hydrocarbon radical having 2 to 12, preferably 2 to 8, particularly preferably 2 to about 6 (lower alkynyl), carbon atoms with essentially one triple bond. The propynyl and butynyl radicals may be mentioned as examples in this case.

In accordance with the invention, cycloalkyl radicals denote in general cyclic saturated hydrocarbon radicals having 4 to 8, preferably 5 and 6, carbon atoms. The following cycloalkyl radicals may be mentioned as examples: cyclobutyl, cyclopentyl, cyclohexyl, cycloheptyl and cyclooctyl.

The alkyl, alkenyl, alkinyl and cycloalkyl radicals $R^4$ and $R^5$ can, if desired, be substituted by further radicals which do not change under the reaction conditions. The following substituents may be mentioned as examples: O-alkyl, S-alkyl, N-dialkylamino, nitro and cyano.

Together with the nitrogen atoms, the radicals $R^4$ and $R^5$ can form a 5-membered or 6-membered ring system which is optionally interrupted by a further heteroatom. O, S and N may be mentioned as further heteroatoms. The following radicals may be mentioned as examples in this case: pyrrolidyl, piperidyl, morpholyl, thiomorpholyl and piperazyl.

In accordance with the invention, the new N-sulphenylated ureas of the formula (II)

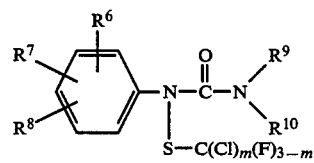

in which
$R^6$ and $R^8$ are identical or different and denote hydrogen, halogen, nitro, cyano, lower alkyl, lower alkoxy, lower alkylmercapto, trihalogenomethyl, trihalogenomethoxy or trihalogenomethylmercapto, $R^9$ and $R^{10}$ represent alkenyl, alkynyl, cycloalkyl or alkyl which is optionally substituted by halogen, cyano, nitro, alkoxy, alkylmercapto or dialkylamino, or together with the nitrogen atom represent a 5-membered or 6-membered ring system which is optionally interrupted by oxygen, sulphur or nitrogen, and m represents the numbers 2 or 3, are preferred.

The following N-sulphenylated ureas may be mentioned as examples: N-(trichloromethanesulphenyl) and N-(fluorodichloromethanesulphenyl) derivatives of N-phenyl-N'-methyl-urea, N-phenyl-N'-dimethyl-urea, N-phenyl-N'-methyl-N-methoxymethyl-urea, N-(4-chlorophenyl)-N'-(2-chloroethyl)-urea, N-(3-trifluoromethylphenyl)-N'-cyclohexyl-urea, N-(3,4-dichlorophenyl)-N'-(6-cyanohexyl)-urea, N-(4-isopropylphenyl)-N'-pyrrolidyl-urea, N-(4-toluidyl)-urea and N-(3-anisidyl)-N'-diallyl-urea.

A process for the preparation of the new N-sulphenylated ureas has also been found, which is characterized in that N-substituted carbamic acid-fluorides of the formula (III)

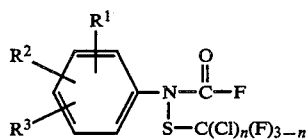
(III)

in which $R^1$ to $R^3$ and n have the meaning given above, are reacted with an amine of the formula (IV)

(IV)

in which $R^4$ and $R^5$ have the meaning given above, in the presence of a diluent and of an acid-binding agent.

The process according to the invention can be illustrated by the following equation:

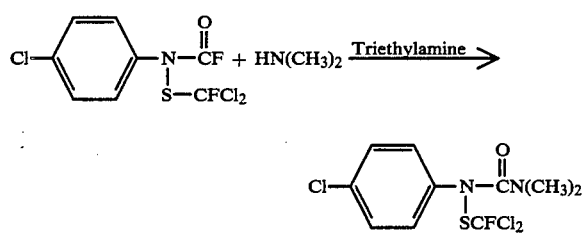

The N-sulphenylated carbamic acid-fluorides for the process according to the invention are in themselves known (German Auslegeschrift No. 1,297,095), and can be prepared from arylcarbamic acid-fluorides and trihalogenomethanesulphenyl chloride in the presence of an acid-binding agent.

The N-(trichloromethanesulphenyl)- and N-(fluorodichloromethanesulphenyl)-carbamic acid-fluorides of aniline, 2-chloro-aniline, 3,4-dichloroaniline, 3-nitroaniline, 4-toluidine, 4-isopropyl-aniline, 3-chloro-4-methoxyaniline, 2-chloro-4-methyl-mercaptoaniline, 2-chloro-4-trifluoromethylaniline, 4-difluoro-chloromethylaniline, 3-chloro-4-trifluoromethoxyaniline and 3-trifluoromethylmercaptoaniline may be mentioned as examples.

The amines of the formula (IV) are in themselves known, and can be prepared, inter alia, in a manner which is in itself known, by alkylation of ammonia. The following amines may be mentioned as examples: methylamine, ethylamine, isopropylamine, allylamine, 2-methoxyethylamine, 2-ethylmercaptoethylamine, neopentylamine, isooctylamine, 2-chloroethylamine, 6-cyanohexylamine, dimethylamine, diallylamine, dibutylamine, cyclopentylamine, cyclohexylamine, pyrrolidine, piperidine, morpholine, thiomorpholine, piperazine, 1,1-dimethylpropin-2-yl-amine and 1,1-diethylpropin-2-yl-amine.

In general, 1 to 2.2 mols of the amine, relative to 1 mol of the N-substituted carbamic acid-fluoride, are employed for the process according to the invention.

The following may be mentioned as examples of diluents for the process according to the invention: hydrocarbons, such as toluene or xylene, chlorohydrocarbons, such as dichloromethane or chlorobenzene, ethers, such as dioxane, ketones, such as acetone, alcohols, such as methanol, or water.

The following may be mentioned as examples of acid-binding agents for the process according to the invention: tertiary amines, such as triethylamine, dimethylbenzylamine and pyridine, inorganic bases, such as sodium hydroxide, sodium or potassium carbonate or bicarbonate, or an excess of the amine of the formula (IV) to be used.

The acid-binding agents are employed in general in an amount of 1 to 2 mols, preferably 1.0 to 1.2 mols relative to 1 mol of the N-substituted, carbamic acid-fluoride.

The reaction temperature for the process according to the invention can be varied within a wide range, in general, the reaction is carried out in the temperature range of 0° to 100° C., preferably from 20° to 50° C.

However, one can also employ slightly reduced or elevated pressures.

The process according to the invention can be carried out, for example, as follows.

The N-substituted carbamic acid-fluoride is dissolved in a diluent. The amine is added to this solution and the mixture is stirred at the particular reaction temperature. The reaction product is precipitated during this process, and is isolated in a conventional manner, for example by crystallization.

The N-sulphenylated ureas according to the invention can be used as active compounds for combating microorganisms. Bacteria, fungi, yeasts, algae and slimeforming microbes may be mentioned as microorganisms. Preferably, the active compounds according to the invention are active against fungi, in particular against wood-discolouring fungi and wood-destroying fungi (Basidiomycetes), and against slimeforming organisms.

The N-sulphenylated ureas according to the invention can be used as active compounds for combating these microorganisms, in particular in industrial materials and in plant protection.

Industrial materials are non-living materials which have been prepared for use in industry. For example industrial materials which are to be protected by active compounds according to the invention against microbial modification and destruction can be adhesives, glues, papers and cardboards, textiles, leather, wood, lumber, coating compositions, building materials, rubber and plastic articles, cooling lubricants, and other materials which can be decomposed by microorganisms. Within the scope of the materials to be protected, parts of production plants, for example cooling water circulation systems, which can be adversely affected by microorganisms may also be mentioned. Industrial materials, preferably coating and impregnating compositions for wood, may be mentioned within the scope of the present invention.

Microorganisms of the following genera may be mentioned as examples of microorganisms which can cause degradation or modification of the industrial materials: Alternaria, such as *Alternaria tenuis,* Aspergillus, such as *Aspergillus niger,* Chaetomium, such as *Chaetomium globosum,* Coniophora, such as *Coniophora cerebella,* Lentinus, such as *Lentinus tigrinus,* Penicillium, such as *Penicillium glaucum,* Polyporus, such as *Polyporus versicolor,* Aureobasidium, such as *Aureobasidium pullulans,* Sclerophoma, such as *Sclerophoma pityophila* and Staphylococcus, such as *Staphylococcus aureus.*

Depending on their field of use, the substances according to the invention can be converted to the customary formulations, such as solutions, emulsions, suspensions, powders, pastes and granules.

These can be produced in a manner which is in itself known, for example by mixing the active compounds with an extender which consists of liquid solvent and/or solid carriers, optionally with the use of surface-active agents, such as emulsifiers and/or dispersing agents, and, for example, when extenders are used, organic solvents can be employed as auxiliary solvents, if appropriate.

Organic solvents for the active compounds can, for example, be alcohols, such as lower aliphatic alcohols, preferably ethanol or isopropanol, or benzyl alcohol ketones, such as acetone or methyl ethyl ketone, liquid hydrocarbons, such as petrol fractions, and chlorinated hydrocarbons, such as 1,2-dichloroethane.

The use concentrations of the substances according to the invention depend on the type and occurrence of the microorganisms to be combated, and on the composition of the material to be protected. The optimum use amount can be determined by test series. In general, the use concentrations are in the range from 0.001 to 5% by weight, preferably from 0.05 to 1.0% by weight, relative to the material to be protected.

The new active compounds according to the invention can also be present as a mixture with other known active compounds. The following active compounds may be mentioned as examples: benzimidazolyl-methyl-carbamates, tetramethyl-thiuram disulphide, Zn salts of dialkyldithiocarbamates, 2,3,5,6-tetrachloro-isophthalonitrile, thiazolylbenzimidazole, N-cyclohexyl-N-methoxy-2,5-dimethyl-3-furamide, mercaptobenzothiazole and phenol derivatives, such as 2-phenyl-phenol and (2,2'-dihydroxy-5,5'-dichloro)-diphenylmethane.

The N-sulphenylated ureas according to the invention can also be used as plant protection agents, in particular for combating fungi.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

They display a particularly good activity against parasitic fungi on above-ground parts of plants, such as, for example, against the apple scab causative organism (*Fusicladium dendriticum*) and against the glume blotch of wheat causative organism (*Leptosphaeria nodorum*). They also exhibit an activity against rice diseases (causative organisms, for example, *Pyricularia oryzae* and *Pellicularia sasakii*). In addition, they are active against diseases originating from the seed, such as, for example, against rough-spored bunt of wheat (*Tilletia caries*).

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main. aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water, by liquefied gaseous extenders or carriers are meant liquids which are gaseous at normal temperature and under normal pressure, for example aerosol propellants, such as halogenated hydrocarbons as well as butane, propane, nitrogen and carbon dioxide, as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolyzation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellants, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporising, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g/kg of seed, preferably 0.01 to 10 g, are generally required.

For the treatment of soil, active compound concentrations of 0.00001 to 0.1% by weight, preferably 0.0001 to 0.02%, are required at the place of action.

PREPARATION EXAMPLES

Example 1

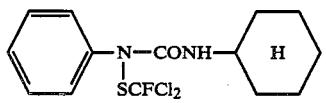

20 g (0.073 mol) of N-phenyl-N-(fluorodichloromethanesulphenyl)-carbamic acid-fluoride are dissolved in 200 ml of dioxane. 14.6 g (1.475 mols) of cyclohexylamine are added dropwise to this solution at room temperature, and the temperature is allowed to increase to 38° C. The mixture is stirred for about 30 minutes, and the reaction product is precipitated with water. It is filtered off under suction, washed with water and dried.

Yield: 24 g=93% of theory; m.p. 98°–100° C.

Examples 2 to 17

The following N-substituted ureas are prepared in an analogous manner.

$$Ar-N(SCFCl_2)-CO-N(R^1)(R^2)$$

| No. | Ar | $R^1$ | $R^2$ | m.p. ($n_D^{20}$) |
|---|---|---|---|---|
| 2 | $C_6H_5$ | $CH_3$ | $CH_3$ | 46–50° C. |
| 3 | 3,4-Cl—$C_6H_3$— | $CH_3$ | $CH_3$ | 100° C. |
| 4 | 4-Cl—$C_6H_4$ | $CH_3$ | $CH_3$ | 86–88° C. |
| 5 | $C_6H_5$ | H | H | 141–142° C. |

-continued $$Ar-N(SCFCl_2)-CO-N(R^1)(R^2)$$

| No. | Ar | $R^1$ | $R^2$ | m.p. ($n_D^{20}$) |
|---|---|---|---|---|
| 6 | 2-Cl—$C_6H_4$ | H | H | 98–100° C. |
| 7 | 4-Cl—$C_6H_4$ | H | H | 142–144° C. |
| 8 | 3,5-Cl—$C_6H_3$ | H | H | 126–127° C. |
| 9 | 3,5-Cl—$C_6H_3$ | $CH_3$ | H | 137–138° C. |
| 10 | 3,5-Cl—$C_6H_3$ | $CH_3$ | $CH_3$ | 122–123° C. |
| 11 | $C_6H_5$ | $CH_3$ | H | 132° C. |
| 12 | 3-Cl—$C_6H_4$ | H | H | 95–99° C. |
| 13 | 3-Cl—$C_6H_4$ | $CH_3$ | H | 126–128° C. |
| 14 | 3-Cl—$C_6H_4$ | $CH_3$ | $CH_3$ | (1.5681) |
| 15 | 4-Cl—$C_6H_4$ | $CH_3$ | H | 128–129° C. |
| 16 | 3,4-Cl—$C_6H_3$ | H | H | 139–140° C. |
| 17 | 3,4-Cl—$C_6H_3$ | $CH_3$ | H | 125–128° C. |

Example 18

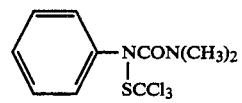

28.8 g (1/10 mol) of N-phenyl-N-(trichloromethanesulphenyl)-carbamic acid-fluoride are dissolved in 100 ml of toluene, and 46 ml of a 20% strength solution of dimethylamine in toluene are added at 20° to 30° C., while cooling. The reaction solution is washed with water, the organic phase is dried and the toluene is stripped off in vacuo. The crystalline residue (29 g) is recrystallized from naphtha.

Yield: 27 g=86% of theory, m.p. 65°–67° C.

Examples 19 and 20

The following compounds are obtained in an analogous manner:

$$C_6H_5-N(SCCl_3)-CO-N(R^1)(R^2)$$

| No. | $R^1$ | $R^2$ | m.p. |
|---|---|---|---|
| 19 | H | H | 145–146° C. |
| 20 | $CH_3$ | H | 147–148° C. |

USE EXAMPLES

Example 20

To demonstrate the activity against fungi, the minimum inhibitory concentrations (MIC) of the active compounds according to the invention are determined.

Active compounds according to the invention are added, in concentrations of 0.1 mg/liter to 5,000 mg/liter, to an agar prepared from bierwort and peptone. After the agar has solidified, contamination with pure cultures of the test organisms listed in the table is effected. After storage for 2 weeks at 28° C. and 60 to 70% relative atmospheric humidity, the MIC is determined. The MIC is the lowest concentration of active compound at which the microbe species used exhibits no growth; it is given in Table I below.

Table I:
Data on the MIC values in mg/liter, for the action of N-sulphenylated ureas of the following formula on fungi:

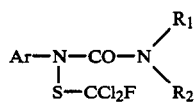

TABLE 1

| Substance | | | MIC in mg/l | | | | | | | | |
|---|---|---|---|---|---|---|---|---|---|---|---|
| Ar | $R_1$ | $R_2$ | Alternaria tenuis | Aspergillus niger | Aureobasidium pullulans | Chaet. glob. | Coniophora puteana | Lentinus tigrinus | Penicil. glaucum | Polyporus versicolor | Sclerophona pityophila |
| $C_6H_5$ | H | H | 20 | 100 | 20 | 100 | 5 | 15 | 100 | 100 | 20 |
| 4-Cl—$C_6H_5$ | H | H | 3.5 | 10 | 5 | 35 | 0.5 | 1 | 50 | 15 | 10 |
| 3-Cl—$C_6H_5$ | H | H | 7.5 | 35 | 10 | 75 | 1 | 1 | 50 | 10 | 10 |
| 3,4-Cl—$C_6H_5$ | H | H | 1.5 | 10 | 10 | 15 | 0.5 | 1 | 20 | 2 | 10 |
| 3,5-Cl—$C_6H_5$ | H | H | 3.5 | 50 | 2 | 10 | 1.5 | 1 | 10 | 10 | 5 |
| $C_6H_5$ | H | $CH_3$ | 100 | 350 | 150 | 200 | 20 | 75 | 500 | 350 | 100 |
| 3-Cl—$C_6H_5$ | H | $CH_3$ | 7.5 | 10 | 10 | 20 | 0.5 | 1 | 200 | 20 | 10 |
| 4-Cl—$C_6H_5$ | H | $CH_3$ | 15 | 50 | 20 | 20 | 1 | 2 | 20 | 35 | 15 |
| 3,4-Cl—$C_6H_5$ | H | $CH_3$ | 1.5 | 10 | 5 | 10 | 0.3 | <1 | 50 | 10 | 5 |
| 3,5-Cl—$C_6H_5$ | H | $CH_3$ | 5 | 35 | 2 | 35 | <0.1 | 5 | 75 | 10 | 5 |
| $C_6H_5$ | $CH_3$ | $CH_3$ | 100 | 200 | 35 | 200 | 7.5 | 100 | 200 | 750 | 100 |
| 3-Cl—$C_6H_5$ | $CH_3$ | $CH_3$ | 5 | 20 | 5 | 10 | 0.3 | 1 | 200 | 20 | 10 |
| 3,4-Cl—$C_6H_5$ | $CH_3$ | $CH_3$ | 2 | 20 | 2 | 10 | 1.5 | <1 | 50 | 10 | 15 |
| 3,5-Cl—$C_6H_5$ | $CH_3$ | $CH_3$ | 1 | 20 | 2 | 10 | <0.1 | 1 | 150 | 750 | 1 |

Example 21

(Action against slime organisms)

Compounds according to Table II, each in concentrations from 0.1 to 100 mg/liter in Allens nutrient solution (Arch. Mikrobiol. 17, 34 to 53 (1952)) which contains, in 4 liters of sterile water, 0.2 g of ammonium chloride, 4.0 g of sodium nitrate, 1.0 g of dipotassium hydrogen phosphate, 0.2 g of calcium chloride, 2.05 g of magnesium sulphate, 0.02 g of iron chloride and 1% of caprolactam, are employed dissolved in a small amount of acetone. Shortly beforehand, the nutrient solution is infected with slime organisms (approx. $10^6$ germs/ml) which were isolated from spinning liquid circulations used in polyamide production. Nutrient solutions which have the minimum inhibitory concentration (MIC) or greater active compound concentrations are still completely clear after culture for 3 weeks at room temperature, that is to say the pronounced multiplication of the microbes and formation of slime, which are noticeable after 3 to 4 days in nutrient solutions free of active compound, are suppressed.

The MIC values in Table II are determined in this manner for compounds according to the invention, of the formula below.

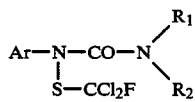

TABLE II

| Substance | | | |
|---|---|---|---|
| Ar | $R_1$ | $R_2$ | MIC in mg/l |
| 3,5-Cl—$C_6H_5$ | H | H | 2 |
| 3,5-Cl—$C_6H_5$ | H | $CH_3$ | 50 |

TABLE II-continued

| Substance | | | |
|---|---|---|---|
| Ar | $R_1$ | $R_2$ | MIC in mg/l |
| 3,5-Cl—$C_6H_5$ | $CH_3$ | $CH_3$ | 2 |

Example 22

Tilletia caries test (wheat)/seed treatment
The active compounds are used as dry dressings.

These are prepared by extending the particular active compound with a ground mineral to give a finely pulverulent mixture, which ensures uniform distribution on the seed surface.

To apply the dressing, the seed, which has been contaminated beforehand with 5 g of chlamydospores of Tilletia caries per kg of seed, is shaken with the dressing in a closed glass flask for 3 minutes.

The seed, on moist loam under a cover of a layer of muslin and 2 cm of moist vermiculite, is exposed to optimum germination conditions for the spores at 10° C. in a refrigerator for 10 days.

10 days after sowing, the germination of spores on the wheat grains is evaluated.

The result of the test is given in Table III, in comparison with the commercially available compound Zineb:

TABLE III

Tilletia caries test (wheat)/seed treatment

| Active compound | Amount of active compound applied in mg/kg of seed | Spore germination in % of the untreated control |
|---|---|---|
| Zineb (for comparison) | 100 | 5.0 |

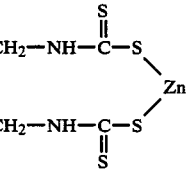

according to the invention:

4,562,208

TABLE III-continued

Tilletia caries test (wheat)/seed treatment

| Active compound | Amount of active compound applied in mg/kg of seed | Spore germination in % of the untreated control |
|---|---|---|
| [phenyl]-N(SCFCl$_2$)-CO-NH$_2$ | 100 | 0.0 |
| 2-Cl-[phenyl]-N(SCFCl$_2$)-CO-NH$_2$ | 100 | 0.0 |
| 4-Cl-[phenyl]-N(SCFCl$_2$)-CO-NH$_2$ | 100 | 0.05 |

Example 23

Leptosphaeria nodorum test (wheat)/protective
Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain in an incubation cabin at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

The clear superiority of active compounds according to the invention in comparison with the commercially available compound zineb is shown in Table IV below:

TABLE IV

Leptosphaeria nodorum test (wheat)/protective

| Active compound | Active compound concentration in the spray liquor in % by weight | Disease infestation in % of the untreated control |
|---|---|---|
| Zineb (for comparison) | 0.025 | 100 |

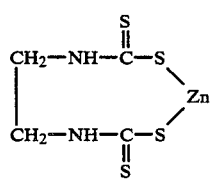

TABLE IV-continued

Leptosphaeria nodorum test (wheat)/protective

| Active compound | Active compound concentration in the spray liquor in % by weight | Disease infestation in % of the untreated control |
|---|---|---|
| according to the invention: | | |
| [phenyl]-N(SCFCl$_2$)-CO-NH-CH$_3$ | 0.025 | 25.0 |
| 2-Cl-[phenyl]-N(SCFCl$_2$)-CO-NH$_2$ | 0.025 | 33.8 |
| 4-Cl-[phenyl]-N(SCFCl$_2$)-CO-NH-CH$_3$ | 0.025 | 0.0 |

Example 24

Venturia test (apple)/protective
Solvent: 4.7 parts by weight of acetone
Emulsifier: 0.3 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabin at 20° C. and 100% relative atmospheric humidity for 1 day.

The plants are then placed in a greenhouse at 20° C. and a relative atmospheric humidity of about 70%.

Evaluation is carried out 12 days after the inoculation.

The clear superiority of the active compounds according to the invention in comparison with the prior art is shown in Table V below:

TABLE V

Venturia test (apple)/protective

| Active compound | Infestation in % at an active compound concentration of 0.0005% |
|---|---|
| for comparison, according to German Offenlegungsschrift 1,193,498 | 22 |

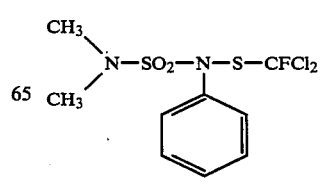

TABLE V-continued

Venturia test (apple)/protective

| Active compound | Infestation in % at an active compound concentration of 0.0005% |
|---|---|
| according to the invention: | |
| 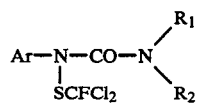 | 6 |
| Cl–C$_6$H$_3$(Cl)–N(S–CCl$_2$F)–CO–NH–CH$_3$ | |
| 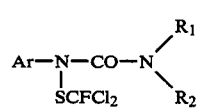 | 7 |
| Cl–C$_6$H$_3$(Cl)–N(S–CCl$_2$F)–CO–N(CH$_3$)$_2$ | |

What is claimed is:

1. A N-sulphenylated urea of the formula $$Ar-N(SCFCl_2)-CO-N(R_1)(R_2)$$

and wherein Ar is 4—Cl—C$_6$H$_5$ or 3,4 di Cl—C$_6$H$_5$ and R$^1$ and R$^2$ are both CH$_3$.

2. A N-sulphenylated urea of the formula

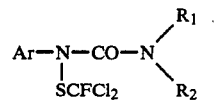

and wherein Ar is 4—Cl—C$_6$H$_5$ or 3,4 di—Cl—C$_6$H$_5$ and R$^1$ is H and R$^2$ is CH$_3$.

3. A microbicide containing an effective microbicidal amount of a N-sulphenylated urea of the formula $$Ar-N(SCFCl_2)-CO-N(R_1)(R_2)$$

and wherein Ar is 4—Cl—C$_6$H$_5$ or 3,4 di—Cl—C$_6$H$_5$ and R$^1$ and R$^2$ are both CH$_3$ and a diluent.

4. A microbicide, containing an effective microbicidal amount of a N-sulphenylated urea of the formula $$Ar-N(SCFCl_2)-CO-N(R_1)(R_2)$$

and wherein Ar is 4—Cl—C$_6$H$_5$ or 3,4 di—Cl—C$_6$H$_5$ and R$^1$ is H and R$^2$ is CH$_3$ and a diluent.

* * * * *